(12) United States Patent
Maki

(10) Patent No.: US 8,932,052 B2
(45) Date of Patent: Jan. 13, 2015

(54) DELIVERY SYSTEMS FOR ORTHODONTIC CHAINS

(71) Applicant: Jeffrey Allan Maki, Laporte, IN (US)

(72) Inventor: Jeffrey Allan Maki, Laporte, IN (US)

( * ) Notice: Subject to any disclaimer, the term of this patent is extended or adjusted under 35 U.S.C. 154(b) by 0 days.

(21) Appl. No.: 14/043,359

(22) Filed: Oct. 1, 2013

(65) Prior Publication Data

US 2014/0093833 A1  Apr. 3, 2014

Related U.S. Application Data

(60) Provisional application No. 61/708,094, filed on Oct. 1, 2012.

(51) Int. Cl.
*A61C 3/00* (2006.01)
*A61C 7/30* (2006.01)

(52) U.S. Cl.
CPC ...................................... *A61C 7/306* (2013.01)
USPC ............................................................ 433/3

(58) Field of Classification Search
USPC ............ 433/3–18; 221/10, 25, 30, 74, 76, 22, 221/23, 32, 197, 206, 207, 217, 222, 255, 221/277, 287; 225/10–16
See application file for complete search history.

(56) References Cited

U.S. PATENT DOCUMENTS

| 5,851,347 | A | * | 12/1998 | Rodriguez | .................... 156/576 |
| 6,789,594 | B1 | | 9/2004 | Chen | |
| 7,320,351 | B2 | | 1/2008 | Chern | |
| 7,441,581 | B2 | | 10/2008 | Pitzen | |
| 7,845,381 | B2 | | 12/2010 | Liu | |
| 8,100,042 | B2 | | 1/2012 | Chen | |
| 2011/0271811 | A1 | * | 11/2011 | Sheffield | ........................ 83/649 |

* cited by examiner

*Primary Examiner* — Cris L Rodriguez
*Assistant Examiner* — Matthew Saunders
(74) *Attorney, Agent, or Firm* — Hartman Global IP Law; Gary M. Hartman; Michael D. Winter

(57) ABSTRACT

Delivery systems suitable for dispensing orthodontic chains. Such a delivery system includes a housing assembly adapted to enclose an orthodontic chain within an interior cavity of the delivery system defined by and between individual components of the housing assembly. The delivery system further includes an advancement mechanism adapted to engage the orthodontic chain within the interior cavity and dispense the orthodontic chain from the delivery system, a cutting mechanism adapted to cut the orthodontic chain while disposed within the interior cavity, and an exit through which the orthodontic chain exits the interior cavity.

15 Claims, 8 Drawing Sheets

DELIVERY SYSTEMS FOR ORTHODONTIC CHAINS

CROSS REFERENCE TO RELATED APPLICATIONS

This application claims the benefit of U.S. Provisional Application No. 61/708,094, filed Oct. 1, 2012, the contents of which are incorporated herein by reference.

BACKGROUND OF THE INVENTION

The present invention generally relates to elastic orthodontic chains of types used by dental professionals. More particularly, this invention relates to a handheld, self-contained delivery system for orthodontic chains.

Orthodontic chain materials are used by dental professionals in conjunction with dental braces as a source of force in correcting irregularities in the position of a patient's teeth. The chains are formed of elastic cords and used to hold arch wires into brackets and to move teeth. Typically, the chains are often made of polyurethane or similar elastic material and sold on bobbins or spools.

An important aspect of elastic orthodontic chains is that they remain sterile so as to avoid causing an infection once placed in a patient's mouth. Unfortunately, elastic orthodontic chains are not easily disinfected due to their polymeric compositions. Most sterilization and disinfection chemicals commonly used in dental offices affect and/or deteriorate the elastic material of an orthodontic chain resulting in decreased tensile strength and life span. Consequently, elastic orthodontic chains are typically kept sterile by enclosing them within hygienic containers. These containers are often in the form of dispensers capable of holding multiple bobbins of chain while protecting the exposed chain from outside contaminates. However, orthodontic chain dispensers tend to be bulky and not easily transported. Further, they do not always include a cutting mechanism, resulting in the need to dispense the chain using two hands and a less sanitary dispensing process.

Accordingly, there is a need for dispensers of elastic orthodontic chains that are not bulky, are relatively easy to use, and capable of maintaining sanitary conditions of chains prior to and during dispensing.

BRIEF DESCRIPTION OF THE INVENTION

The present invention provides delivery systems suitable for dispensing orthodontic chains.

According to a first aspect of the invention, a delivery system includes a housing assembly adapted to enclose an orthodontic chain within an interior cavity of the delivery system defined by and between individual components of the housing assembly. The delivery system further includes an advancement mechanism adapted to engage the orthodontic chain within the interior cavity and dispense the orthodontic chain from the delivery system, a cutting mechanism adapted to cut the orthodontic chain while disposed within the interior cavity, and an exit through which the orthodontic chain exits the interior cavity.

A technical effect of the invention is that the delivery system is configured as a handheld system that is capable of dispensing orthodontic chains quickly, easily, and in a sanitary manner, and preferably enables a chain to be dispensed when operated with a single hand, for example, with the use of a single digit of the hand.

Other aspects and advantages of this invention will be better appreciated from the following detailed description.

DETAILED DESCRIPTION OF THE INVENTION

Figure 1:
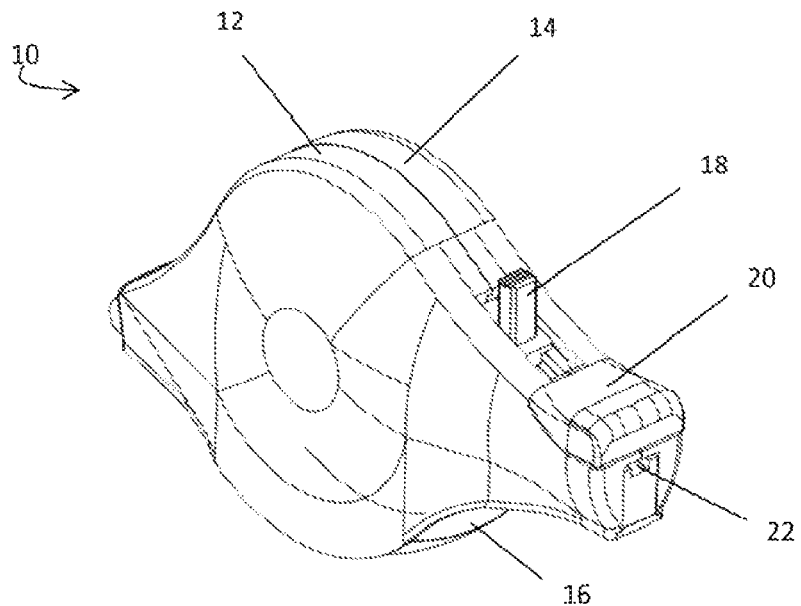
FIGS. 1 through 7 represent a handheld, self-contained delivery system for an orthodontic chain according to a first embodiment of the present invention.

To facilitate the description of embodiments of the invention provided below, relative terms, including but not limited to "front," "rear," "forward," "rearward," "upper," "lower," "above," "below," etc., may be used in reference to the orientation of the invention as represented in certain Figures, and therefore are relative terms but should not be otherwise interpreted as limitations to the operation and use of the invention.

FIGS. 1 through 7 represent a handheld, self-contained delivery system 10 for orthodontic chains according to a first embodiment of the present invention. The delivery system 10 is a hand-held device adapted to disperse and cut specific amounts of orthodontic chain in a sanitary manner. The system 10 is particularly suitable for use in dental offices where the ability to operate an orthodontic chain dispenser with a single hand would provide a significant level of convenience to dental healthcare providers. As represented in FIGS. 1 through 7, the delivery system 10 is an assembly that comprises multiple components. As a nonlimiting example, the embodiment of the system 10 represented in FIG. 1 comprises first and second upper housings 12 and 14, respectively, and a lower housing 16, which form an assembly equipped with an advancement mechanism 18 and a cutter button 20. The advancement mechanism 18 is adapted to advance an orthodontic chain (not shown) disposed within the system 10, and the cutter button 20 is adapted to cut the orthodontic chain after a portion thereof has been dispensed through an exit 22 from an interior cavity of the system 10 defined and enclosed by the housings 12, 14 and 16. The cutter button 20 and a cutting mechanism operated thereby are disposed closer to the exit 22 than the advancement mechanism 18.

Figure 2:
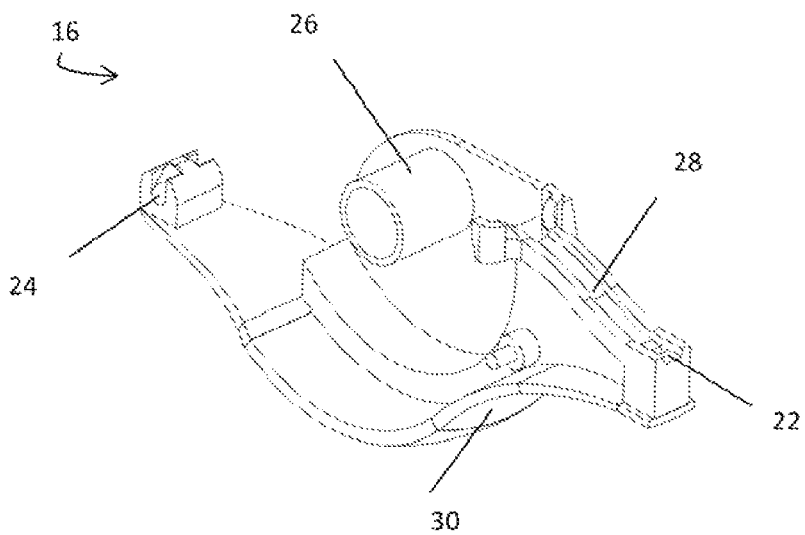
Figure 3:
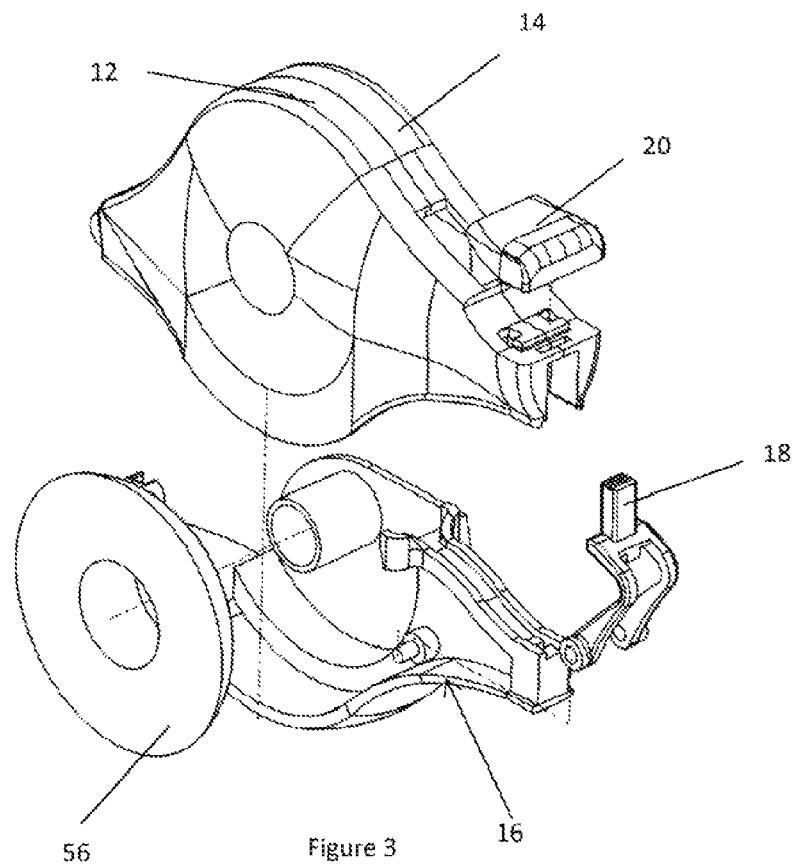

The delivery system 10 of FIGS. 1 through 7 is particularly suitable for dispensing orthodontic chains formed of elastic materials, for example, polyurethane or a similar material, which may contain one or more antibacterial additives. FIG. 3 represents a bobbin 56 of a type on which orthodontic chains are commercially available, wherein the chain is wrapped around the circumference of the bobbin 56 as known in the art. The bobbin 56 may be purchased commercially or fabricated specifically for use in combination with the delivery system 10. In the embodiment represented in FIGS. 1 through 7, a relatively small-sized bobbin 56 is represented of a type commercially available from at least one orthodontics manufacturer. Manufacturers of elastic orthodontic chains typically wind or coil their chains around bobbins of standardized sizes, which limits the size and shape of bobbins that are widely commercially available. However, it is also foreseeable and within the scope of the invention that the bobbin 56 could be designed to have a tailored size and shape specific to a specific type of chain to be dispensed with the delivery system 10. Furthermore, it is foreseeable that chains could be developed that are designed specifically for use with the delivery system 10. For example, the chain may comprise markings that allow a user to measure the chain to a desired length.

Figure 4:
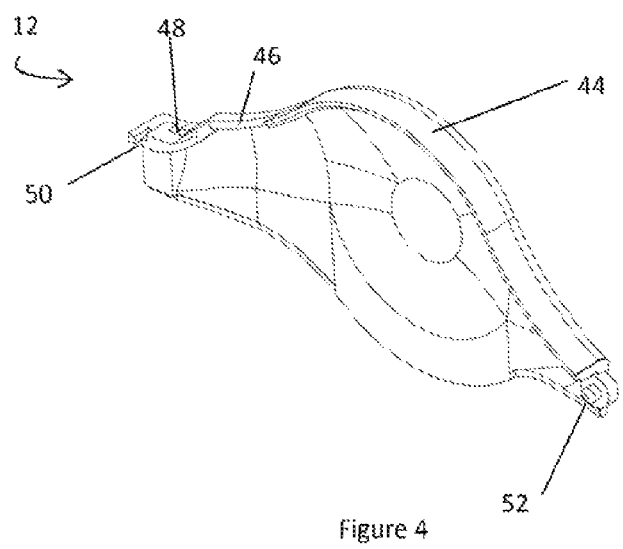
Figure 5:
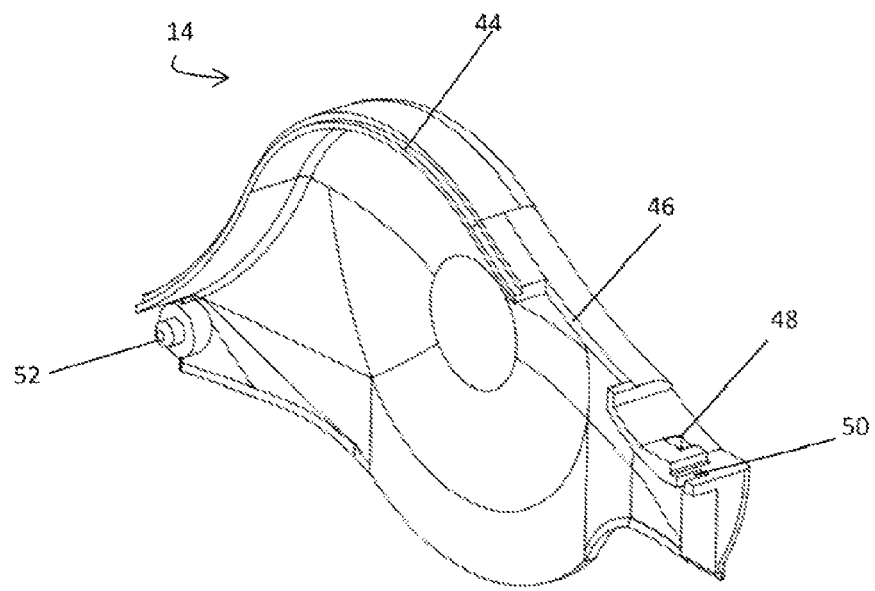
Figure 6:
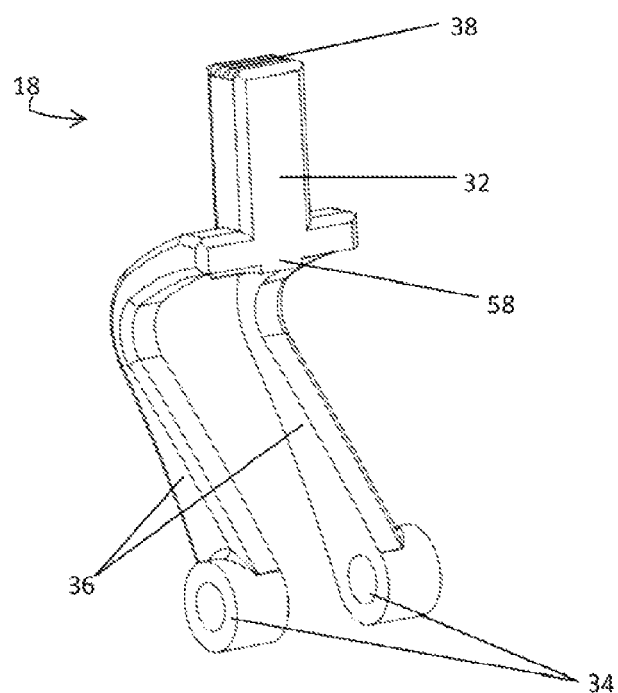
Figure 7:
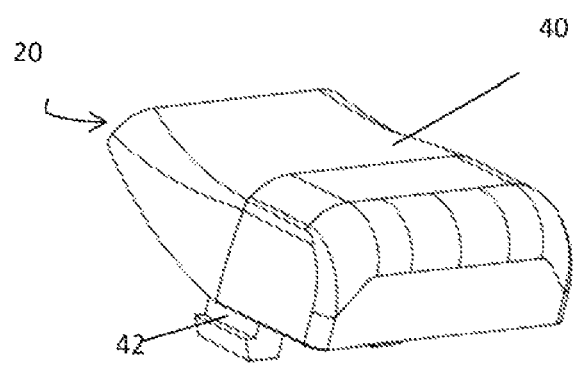

FIG. 3 is a perspective exploded view representing individual external and internal components that, when assembled, yield the delivery system 10 of FIG. 1. FIGS. 2, 4 and 5 represent isolated perspective views of, respectively, the lower housing 16 and the first and second upper housings 12 and 14 of the delivery system 10 of FIG. 1. FIG. 6 represents an isolated view of the advancement mechanism 18, and FIG. 7 represents an isolated view of the cutter button 20. The lower housing 16, upper housings 12 and 14, advancement mechanism 18, and cutter button 20 can be fabricated using a variety of processes such as, but not limited to, injection molding, and are preferably formed of a base material optionally containing one or more antibacterial additives. The base material is preferably capable of being disinfected with standard chemicals commonly found in a dental office.

In the embodiment shown in FIGS. 1 through 7, the lower housing 16 serves as a base structure of the delivery system 10 in that all other components of the system 10 are directly connected to the lower housing 16 and/or are interconnected to each other via the lower housing 16. As represented in FIG. 2, the lower housing 16 comprises a vertical wall from which an axle or hub 26 protrudes into the interior cavity of the system 10. A lower portion of the interior cavity can be seen in FIG. 2. The lower housing 16 further defines a track 28 extending away from the hub 26 toward an end of the system 10, a lower portion of the exit 22 located at the end and aligned with the track 28, and a female connector 24 located at an end of the lower housing 16 opposite the exit 22 relative to the hub 26. The female connector 24 is configured so that the upper housings 12 and 14 can be coupled to the lower housing 16 via complementary connectors 52 of the upper housings 12 and 14 (FIGS. 4 and 5). The hub 26 is configured to couple with a bore of the bobbin 56 to secure the bobbin 56 within the interior cavity of the delivery system 10. The hub 26 enables the bobbin 56 to rotate about the hub 26. In use, a chain dispensed from the bobbin 56 slides over the track 28 as it is dispensed from the bobbin 56 and before exiting the interior cavity of the system 10 through the exit 22.

The upper housings 12 and 14 cooperate with the lower housing 16 to enclose the chain and cutting mechanism (actuated by the cutter button 20) within the interior cavity of the system 10, thereby protecting the chain and cutting mechanism from contamination by outside sources. FIGS. 4 and 5 represent the upper housings 12 and 14 as comprising complementary edges 44 and recesses therein that in the delivery system 10 cooperate to define an opening 46 through which the advancement mechanism 18 is operated. The edges 44 of the upper housings 12 and 14 are adapted to couple and close the interior cavity of the system 10. The upper housings 12 and 14 are further equipped with the aforementioned connectors 52 adapted to couple with the female connector 24 of the lower housing 16 for the purpose of securing the upper housings 12 and 14 to the lower housing 16, thereby enclosing the bobbin 56 therein. The upper housings 12 and 14 also define complementary portions of a blade opening 50 through which a blade (not shown) of the cutting mechanism protrudes and can be actuated by depressing the cutter button 20 to cut an orthodontic chain as it is dispensed from the interior cavity of the system 10 along the track 28 and through the exit 22.

The advancement mechanism 18 serves to control the dispensing of a chain within the system 10. By pressing an advancement grip 38 of the advancement mechanism 18, for example, with the user's thumb, a chain disposed on the track 28 of the lower housing 16 can be pinched between the track 28 and a pinching surface 58 of the advancement mechanism 18 that opposes the track 28. While the chain remains gripped between the track 28 and pinching surface 58, a user may then push the grip 38 toward the exit 22 to cause the chain to be advanced along the track 28 and dispensed from the interior cavity of the system 10 through its exit 22. In addition to the grip 38 and pinching surface 58, the advancement mechanism 18 is represented in FIG. 6 as comprising a column 32 that extends between and interconnects the grip 38 and pinching surface 58, a pair of legs 36 projecting side-by-side from the column 32, and female connectors 34 on the legs 36. The legs 36 are configured as springs that can be partially flexibly collapsed or compressed in a direction generally coinciding with their lengths, enabling the column 32 to be elastically deflected toward the female connectors 34. The female connectors 34 are adapted to couple with complementary male connectors 30 (one of which is visible in FIG. 3) disposed on opposite sides of the track 28 of the lower housing 16 to pivotally secure the advancement mechanism 18 to the lower housing 16. In combination, the legs 36 and connectors 34 effectively define a resiliently flexible pivot by which the advancement mechanism 18 is able to flex into engagement with an orthodontic chain and also pivot for the purpose of pinching/gripping and advancing the chain from the interior cavity of the system 10. Once assembled, the upper housings 12 and 14 enclose the advancement mechanism 18 with the exception of the grip 38 and a portion of the column 32, which protrude through the opening 46 of the upper housings 12 and 14 to enable a user to access and operate the advancement mechanism 18 by pressing the grip 38 downward into the opening 46 and then pivoting the grip 38 toward the exit 22 of the system 10.

The cutter button 20 is preferably spring-actuated and carries a metal cutting blade (not shown) secured beneath the button 20 so as to project through the blade opening 50 and be operable to cut a portion of an orthodontic chain supported on the track 28 within the blade opening 50. The cutting blade can be formed of a metallic material and is preferably sufficiently thin to be capable of precisely cutting the chain. The cutter button 20 is represented in FIG. 7 as having an upper surface 40 and adapted for attachment to the upper housings 12 and 14 after the housings 12 and 14 have been secured to the lower housing 16. More particularly, FIG. 7 represents the cutter button 20 as comprising a pair of male snap connectors 42 adapted to couple with a female snap connector 48 formed by complementary portions of the upper housings 12 and 14. A spring (not shown) or other biasing means can be secured between the cutter button 20 and the first and second upper housings 12 and 14 to bias the cutter button 20 away from the upper housings 12 and 14 to an unactuated or open position and so that, upon a user pressing the surface 40 of the button 20, the cutting blade mounted beneath the button 20 is caused to travel through the blade opening 50 and slice the chain lying in the track 28 at or near the exit 22. A second cutting blade (not shown) can be secured within the track 28 of the lower housing 16 opposing the blade mounted to the cutting button 20. In this manner, cutting of the chain can be performed by a scissor action between the opposing blades. As evident from FIG. 1, the cutting button 20 encloses the cutting mechanism (opposing blades) with the upper housings 12 and 14, thereby internally locating the cutting mechanism entirely within the delivery system 10, such that the risk of contamination of the chain is believed to be significantly reduced.

Once assembled, the delivery system 10 provides a self-contained, hygienic orthodontic chain dispenser that can be easy to use and sanitize. As previously noted, a chain can be dispensed by sliding the advancement mechanism 18 that projects above the upper housings 12 and 14 through the opening 46. Once the chain has been dispensed with the advancement mechanism 18 to a desired length, the cutter button 20 may be pressed to cut the chain. Preferably, the delivery system 10 is formed in a shape and size so as to allow the user to dispense and cut the chain with a single hand, for example, by sequentially operating the advancement grip 38 and cutting button 20 with the same digit (e.g., thumb). Further, the delivery system 10 is preferably shaped to be used by either right- or left-handed users and to be easily transported to eliminate the need to have a centralized location for the delivery system 10.

The delivery system 10 may be reusable in that the bobbin 56 can be replaceable, allowing the installation of a different bobbin 56 on which another chain is wound. In order to accommodate replacement bobbins 56, the first and/or second upper housings 12 and 14 can be adapted to be removed from the lower housing 16 and/or otherwise opened relative to the housing 16. Alternatively, the delivery system 10 may be disposable, with the result that the bobbin 56 is not required to be replaceable. Adapting the delivery system 10 to be disposable may be preferable for sanitation purposes.

A second embodiment is represented in FIGS. 8 through 15 as similar to the first embodiment of FIGS. 1 through 7, though employing a different mechanism by which a user advances and dispenses an orthodontic chain. In view of similarities between the first and second embodiments, the following discussion of FIGS. 8 through 15 will focus primarily on aspects of the second embodiment that differ from the first embodiment in some notable or significant manner. Other aspects of the second embodiment not discussed in any detail can be, in terms of structure, function, materials, etc., essentially as was described for the first embodiment.

Figure 8:
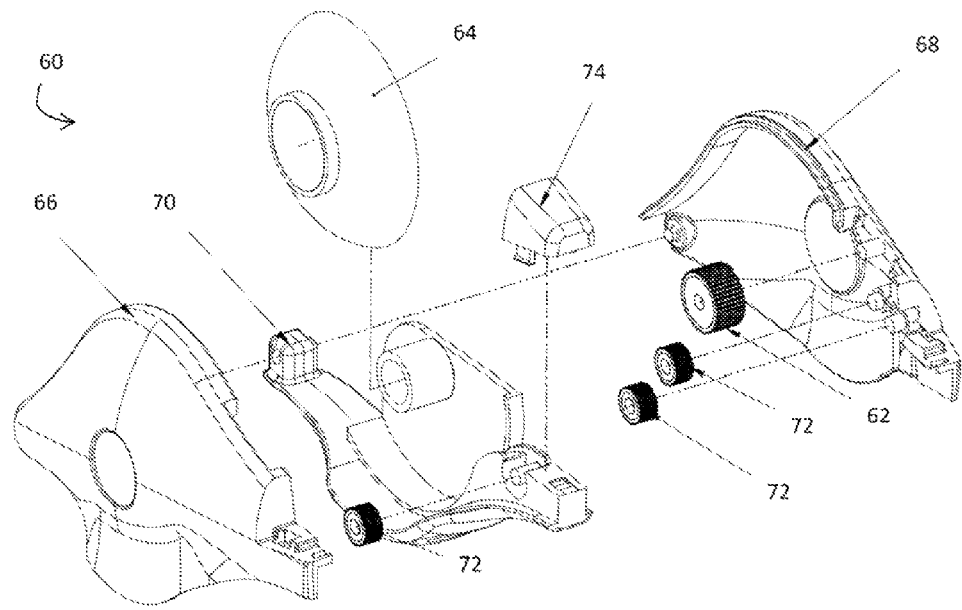
FIGS. 8 through 15 represent a handheld, self-contained delivery system for an orthodontic chain according to a second embodiment of the present invention.
Figure 9:
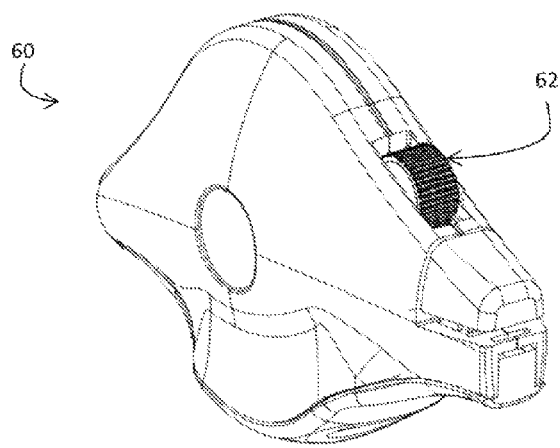
Figure 10:
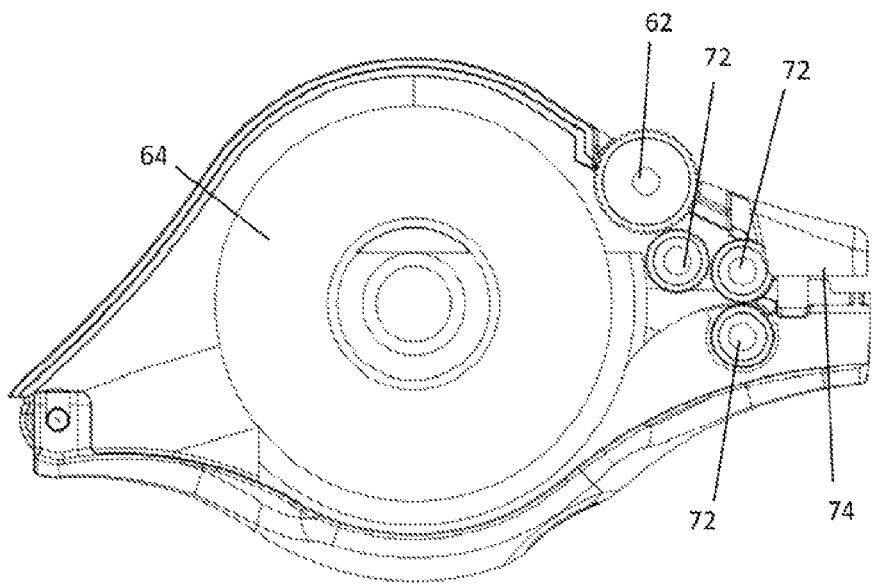
Figure 11:
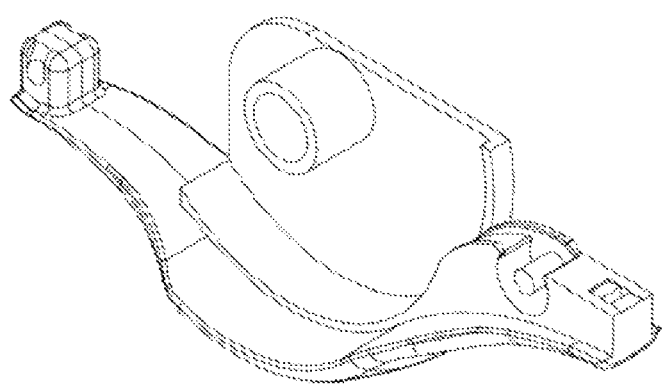
Figure 12:
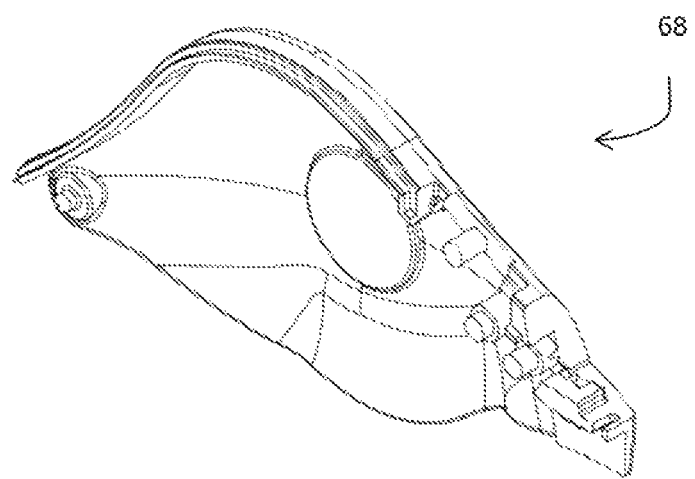

FIG. 8 represents an exploded view of a delivery system 60 which uses a thumb wheel 62 to control the advancement of an elastic orthodontic chain. Similar to the system 10 of FIGS. 1 through 7, the system 60 is configured to use a bobbin 64 around which an orthodontic chain is wrapped, as is conventional in the art. First and second upper housings 66 and 68 and a lower housing 70 can be configured and connected in essentially the same way as described for the housings 12, 14 and 16 of the system 10, that is, the lower housing 70 can be configured as a base that the other components connect to or are connected through. FIG. 8 is a perspective exploded view of the system 60, FIG. 9 is a perspective view of the assembled system 60, FIG. 10 represents a view of the interior cavity of the system 60 and internal components thereof, FIG. 11 is an isolated view of the lower housing 70, and FIG. 12 is an isolated view of the second upper housing 68 (of which the first upper housing 66 may be a mirror image).

Figure 13:
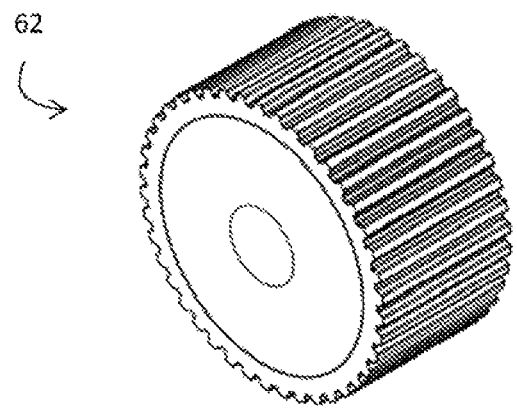
Figure 14:
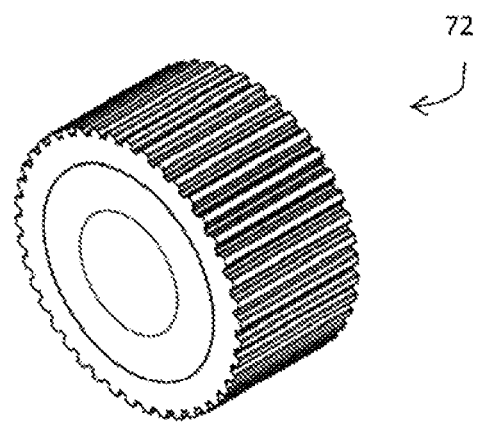
Figure 15:
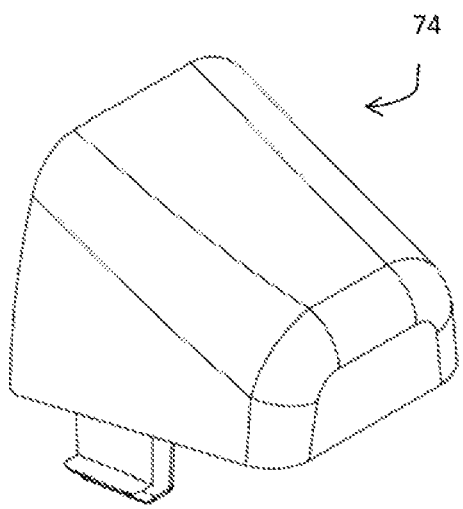

A distinctive feature of the delivery system 60 is that the upper housings 66 and 68 do not enclose an advancement mechanism 18 of the type represented for the system 10, but instead the system 60 makes use of the aforementioned thumb wheel 62. In FIGS. 8, 10, 11 and 12, it should be evident that the thumb wheel 62 and a series of advancement wheels 72 are secured on separate axles or hubs projecting from one of the housings 66, 68 or 70. In the embodiment of FIGS. 8 through 15, a user is able to roll the top of the thumb wheel 62 backwards (away from the exit) to advance an orthodontic chain along what is effectively a serpentine path within the system 60 defined by and between the thumb wheel 62 and an opposing first of the advancement wheels 72 and then between two additional advancement wheels 72 located closer to the exit, as evidenced by FIG. 10. In the absence of a chain, the thumb wheel 62 opposes and engages the first advancement wheel 72, which drives a second advancement wheel 72 located closer to the exit, which in turn drives a third advancement wheel 72 located below the second wheel 72. In this manner, by rotating the thumb wheel 62 the advancement wheels 72 are able to engage and advance the chain toward and through the exit of the system 60. As the user continues to roll the thumb wheel 62, the chain is advanced between a pair of cutting blades (not shown) and then out through the exit 22 of the delivery system 60. As in the previous embodiment, a cutter button 74 can be depressed to activate one of the cutting blades, causing the blades to operate together as a cutting mechanism. FIGS. 13, 14, and 15 are isolated views of the thumb wheel 62, one of the advancement wheels 72, and the cutter button 74, respectively.

While the invention has been described in terms of preferred embodiments, it is apparent that other forms could be adopted by one skilled in the art. For example, the delivery systems 10 and 60 could differ in appearance and construction from the embodiments shown in the Figures, the functions of each component of the delivery systems 10 and 60 could be performed by components of different construction but capable of a similar (though not necessarily equivalent) function, and appropriate materials could be substituted for those noted. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention. Therefore, the scope of the invention is to be limited only by the following claims.

The invention claimed is:

1. A delivery system for dispensing an orthodontic chain, the delivery system comprising:
 a housing assembly enclosing an orthodontic chain within an interior cavity of the delivery system defined by and between individual components of the housing assembly;
 an advancement mechanism that engages the orthodontic chain within the interior cavity and dispenses the orthodontic chain from the delivery system;
 a cutting mechanism that cuts the orthodontic chain at a location on the orthodontic chain disposed within the interior cavity; and
 an exit through which the orthodontic chain exits the interior cavity.

2. The delivery system according to claim 1, wherein the housing assembly comprises a lower housing and first and second upper housings secured to the lower housing and enclosing the orthodontic chain within the interior cavity defined by and between the first and second upper housings and the lower housing.

3. The delivery system according to claim 1, wherein the cutting mechanism comprises a cutter button that operates the cutting mechanism to cut the orthodontic chain.

4. The delivery system according to claim 3, wherein the cutter button is proximate the advancement mechanism to enable sequential dispensing and cutting of the orthodontic chain with a singe digit of a user's hand.

5. The delivery system according to claim 1, wherein the cutting mechanism is disposed closer to the exit than the advancement mechanism.

6. The delivery system according to claim 1, further comprising a bobbin within the interior cavity of the delivery system and on which the orthodontic chain is wound, and a hub on which the bobbin is rotatably mounted within the interior cavity.

7. The delivery system according to claim 1, wherein the advancement mechanism comprises a thumb wheel and at least one advancement wheel gripping the orthodontic chain, wherein rotating the thumb wheel advances the orthodontic chain from the interior cavity of the delivery system.

8. The delivery system according to claim 7, further comprising a serpentine path within the interior cavity and along which the orthodontic chain is disposed and the orthodontic chain is gripped by the at least one advancement wheel.

9. The delivery system according to claim 1, wherein the housing assembly is formed in a shape and size so as to be held in a first hand of a user and the advancement mechanism and cutting mechanism are configured to be operated with the first hand and without a second hand of the user while the user is holding the housing assembly in the first hand.

10. The delivery system according to claim 9, wherein the advancement mechanism and cutting mechanism are configured to be operated with a single digit of the first hand while the user is holding the housing assembly in the first hand.

11. The delivery system according to claim 9, wherein the cutting mechanism comprises at least one cutting blade mounted beneath the cutter button.

12. The delivery system according to claim 1, wherein the housing assembly comprises a track on which the orthodontic chain is disposed and against which the orthodontic chain is gripped or pinched by the advancement mechanism.

13. The delivery system according to claim 1, wherein the advancement mechanism comprises a grip that protrudes from the interior cavity of the delivery system, a pinching surface adapted to pinch the orthodontic chain, and a pivot by which the advancement mechanism is able to grip the orthodontic chain with the pinching surface and then pivot to advance the orthodontic chain from the interior cavity of the delivery system.

14. The delivery system according to claim 13, wherein the pivot comprises flexible legs by which the advancement mechanism flexes into engagement with the orthodontic chain for the purpose of pinching the orthodontic chain and then pivots for the purpose of advancing the orthodontic chain from the interior cavity of the system.

15. The delivery system according to claim 14, further comprising a track within the interior cavity and on which the orthodontic chain is disposed and against which the orthodontic chain is pinched by the pinching surface.

* * * * *